United States Patent [19]

Pfaender et al.

[11] 3,951,741

[45] Apr. 20, 1976

[54] PROCESS AND APPARATUS FOR THE SYNTHESIS OF PEPTIDES BY USE OF N-CARBOXYANHYDRIDES

[76] Inventors: Peter Pfaender, Steinwaldstrasse 64, 7 Stuttgart 70; Helmut Pratzel, Leonrodstrasse 62, 8 Munich 19; Hartmut Blecher, Kauzenhecke 15, 7 Stuttgart-Degerloch 70, all of Germany

[22] Filed: July 3, 1974

[21] Appl. No.: 485,728

[30] Foreign Application Priority Data

July 10, 1973 Germany............................ 2334930
Apr. 8, 1974 Germany............................ 2416941

[52] U.S. Cl......................... 195/29; 260/112.5 R; 23/253 A; 23/285
[51] Int. Cl.²............... C12D 13/00; C07C 103/52
[58] Field of Search.................... 260/112.5; 195/29

[56] References Cited
UNITED STATES PATENTS

| | | | |
|---|---|---|---|
| 3,531,258 | 9/1970 | Merrifield et al................ | 260/112.5 |
| 3,557,077 | 1/1971 | Brunfeldt et al................ | 260/112.5 |
| 3,647,390 | 3/1972 | Kubodera et al................ | 260/112.5 |
| 3,715,190 | 2/1973 | Park et al. ........................ | 260/112.5 |
| 3,725,010 | 4/1973 | Penhast............................ | 260/112.5 |
| 3,819,607 | 6/1974 | Heuser et al..................... | 260/112.5 |
| 3,846,399 | 11/1974 | Hirschmann et al............ | 260/112.5 |

OTHER PUBLICATIONS

Halstrom et al., "Peptides 1972," H. Hanson and H. Jakubke, Eds., North Holland Pub. Co., Amsterdam, 1973, pp. 173–179.

*Primary Examiner*—Lewis Gotts
*Assistant Examiner*—Reginald J. Suyat
*Attorney, Agent, or Firm*—Townsend and Townsend

[57] ABSTRACT

Method and apparatus are provided for preparing polypeptides by conjugating arginine as an end group to a polyethyleneimine water soluble polymer, stepwise addition of amino acids as their N-carboxyanhydrides to prepare the desired polypeptide, enzymatic cleavage of the polypeptide with the arginine group from the polyethyleneimine and enzymatic cleavage of the arginine to provide the desired polypeptide. An automated apparatus is provided for performing the above process.

10 Claims, 6 Drawing Figures

PROCESS AND APPARATUS FOR THE SYNTHESIS OF PEPTIDES BY USE OF N-CARBOXYANHYDRIDES

This invention relates to a process for the synthesis of peptides by the N-carboxyanhydride method, in which individual distinct amino acids are stepwise linked by reacting in the aqueous phase N-carboxyanhydrides of the amino acids in their free form or in the form of protected derivatives of the additional functional groups, which reaction is optionally performed by use of a polymer water-soluble carrier. The invention further concerns an apparatus for the performance of the present process.

The invention especially concerns a process for the synthesis of peptides by use of the N-carboxyanhydride method or arginyl-polyethyleneimine as a water-soluble carrier.

It is known, that by use of the N-carboxyanhydride method at pH 10.2 homologeous and heterologous peptides may be synthesized stepwise in a one reactor process.

The method is based on the following principle:

Herein, R, R' represent any rest derived from a naturally occurring or synthetic amino acid in D-, L- or racemic form. It is, however, necessary to introduce protecting groups removable in a later stage, such as a carbobenzoxy, benzyl, trimethylsilyl groups in third functional groups, which may be present additionally, e.g. $H_2N-$, $HS-$, $HO-$ (such as with lysine, cysteine, serine). Protecting groups are not needed for carboxy- and guanidinium-third functional groups (such as with aspartic acid and arginine).

may be only used with a free carboxyl end group, when the reaction is performed in absence of a carrier. The N-carboxyanhydrides of histidine and $N^{im}$-benzyl-histidine have not been obtained upto now.

By the reaction of a N-carboxyanhydride of an amino acid (NCA I) with an amino acid at 0°C, a peptide carbamate is formed as an alkali stabile intermediate, which on acidification to pH 3-4 at 20°C undergoes a fast decomposition and forms $CO_2$ and the dipeptide. In that manner a tripeptide may be synthesized from the carboxyl end group by adjusting the reaction mixture to pH 10.2 and adding another N-carboyanhydride (NCA II).

It is further known that in this reaction byproducts are formed
1. by the hydrolysis of the N-carboxyanhydrides used to the corresponding free amino acids which offer additional connection points in the following reaction step;
2. by the polycondensation of the N-carboxyanhydrides at an excessive pH;
3. by the formation of hydantoic acids $Ho_2-CH-(R)-NH-CH_2-(R')-CO_2H$;
4. by blocking the amino group of free amino acids caused by carboxylate interchange, when the pH values are too low;
5. by the formation of "overreaction" products (carboxylate interchange at too small pH values, where A-A-B-C is formed in place of A-B-C, wherein A, B and C represent amino acid units of a peptide in the order from the amino end group to the carboxyl end group).

It is further known, that it is possible after each synthesis step to remove low molecular undesired products which are not bound to the carrier, when the water soluble carrier arginyl-polyethyleneimine is used as a starting compound of the peptide synthesis with N-carboxanhydrides.

For the performance of the synthesis it is essential that the N-carboxyanhydrides are distributed as fast as possible in the overall volume of the reaction mixture and that the H-ions being formed are immediately neutralized, so as to prevent practically any deviation from pH 10.2. The above-mentioned reaction conditions may not be maintained when the pH value is controlled manually which causes lower yield. The synthesis of longer peptide chains without carrier, which process was used upto now, has not been possible without intermediate purification.

It is an object of the invention to synthesize peptides with a greater chain length as has been possible up to now, to increase the yield of the peptide synthesis according to the N-carboxyanhydride method remarkably, to accelerate the synthesis procedure and to facilitate reproducable synthesis results.

This invention concerns a process for the synthesis of peptides by the use of N-carboxyanhydrides on the water soluble carrier arginyl-polyethyleneimine (poly(-monopeptide)-polyethyleneimine, wherein the water soluble carrier arginyl-polyethylencimine is formed by the synthesis from polyethyleneimine and the N-carboxyanhydride of arginine-hydrobromide and purified by dialysis and wherein amino acids are stepwise linked to that carrier in form of their unprotected N-carboxyanhydrides or their N-carboxyanhydrides with suitably protected third functional groups, after which addition an intermediate purification step is performed, whereby a peptide chain with the desired sequence of amino acid units is linked to that carrier poly(n-peptide)-polyethyleneimine, polyethyleneimine being subsequently split enzymatically from that peptide chain by trypsin.

The invention further concerns a process for the synthesis of peptides with the use of N-carboxyanhydrides, wherein individual distinct amino acids are stepwise linked by the reaction of the N-carboxyanhydrides of the amino acids in their free form or in form of the protected derivatives of the third functional groups with amino acids in the aqueous phase, optionally with the use of a polymer water soluble carrier, and wherein the introduction of the N-carboxyanhydrides of the amino acids, the agitation of the reaction phase, the sampling, the purification by dialysis, the feeding of liquid or gaseous reactants, the removal of $CO_2$, and the control of the pH-value and of the temperature of the reaction mixture are controlled automatically.

According to a preferred embodiment of the present process the H-ions formed on addition of N-carboxyanhydrides of the amino acids to the reaction medium are neutralized, by the addition of titrating agents controlled by a glass electrode placed in the reaction medium, a proportional differential controller electrically connected with the latter, two motor-driven burettes and feeding lines to the reaction medium, so quickly that any deviation from the predetermined pH-value of 10.2 does not exceed ± 0.1 pH-units.

It is further preferred to introduce the N-carboxyanhydrides of the amino acids in sealed capsules into the reaction medium, where the capsules are broken by a high-speed mixer. By that method there is obtained a distribution in the reaction medium, which is favourable for the reaction yield.

It is further possible to blend the N-carboxyanhydrides with dry water-soluble low molecular organic or anorganic inert materials (e.g. sodium chloride or lactose) in finely divided condition and to compress the mixture to form tablets, which are introduced into the reaction mixture. Some N-carboxyanhydrides (such as N-carboxyanhydrides of arginine-hydrobromide, glutamine, asperagine and proline) are more preferably introduced into the reaction chamber immediately before their reaction in solution with dimethylformamide (absolutely dry).

According to a further preferred embodiment of the invention the desired end product is purified from low molecular undesired by-products not fixed to the carrier with the aid of a pump circulation system and a diafiltration device coupled to a control device. The temperature in the reaction chamber is preferably maintained within a range from 0°C to 30°C, especially at about 1°C.

The invention further concerns an apparatus suitable for the performance of the present process, which comprises a reaction chamber, means for introducing the solid N-carboxyanhydrides of the amino acids, agitation means, means for controlling the pH-value, cooling means, means for purifying the high molecular desired end product from lower molecular byproducts, means for feeding the liquid reactants, gas feeding means, sampling means and means for controlling the timing of the reaction.

The invention preferably concerns a process for the stepwise addition of single distinct amino acids to the water soluble carrier arginyl-polyethyleneimine. After synthesis of a desired sequence of amino acids the peptide is cleaved enzymatically from the carrier. Following this cleavage arginine may be removed enzymatically from the carboxyl end of the peptide. All steps of the process take place in aqueous solution:

a. the synthesis of the carrier arginine-polyethyleneimine from polyethyleneimine and the N-carboxyanhydride of arginine;
b. the stepwise addition of single amino acids to the carrier as their N-carboxyanhydrides;
c. the purification of each addition product by dialysis;
d. the enzymatic cleavage of the completed peptide of desired amino acid sequence from the carrier by trypsin;
e. the enzymatic cleavage of arginine from the carboxyl end of the peptide with carboxypeptidase B.

ad a. Arginyl-polyethyleneimine is synthesized by utilizing the well-known procedures of amino acid N-carboxyanhydride preparation and peptide synthesis from amino acids and their N-carboxyanhydrides in aqueous alkaline solution, specifically at pH 10.2, at temperatures of 0°–20°C, specifically at 1°–2°C, and with high-speed stirring, specifically at 10,000 rpm. Any commercially available fully water-soluble polyethyleneimine of molecular weight over 10,000, for example "Polymin P" made by Fluka AG, Buchs, Switzerland, is a suitable starting material.

ad b. Amino acids are linked to the peptide either as the free N-carboxyanhydride or the N-carboxyanhydride with suitably protected third functional groups.

ad c. The purification of arginyl-polyethyleneimine and the intermediates of the stepwise amino acid additions is performed in commercially available equipment, for example an Amicon Hollow-fiber Dialysis Unit and/or a Concentration Unit DC-2, both made by Amicon, Oosterhout, Holland ("Ultrafiltration with Diaflo Membranes", Amicon Publishers, Oosterhout, Holland, 1972).

ad d. The enzymatic cleavage of the completed peptide from the polymer is carried out with tosyl-phenylalanine-chlorketone treated trypsin at 0°–50°C, specifically at 27°C, over a period of 10 minutes–24 hours, specifically 2 hours, and at a pH of 7–9, specifically at pH 8.0.

ad e. The enzymatic removal of arginine from the carboxyl end of the peptide is achieved with the familiar carboxypeptidase B procedure at 27°C, pH 7.5, for 1 hour.

The advantages of the N-carboxyanhydride-arginine-polyethyleneimine procedure are:

1. All steps may be carried out in aqueous solution.
2. The problems of diffusion in the organic solvent system and the mechanical wear of the resin used for peptide synthesis in the so-called Merrifield procedure may be avoided.
3. The high reactivity of N-carboxyanhydrides affords a short reaction time as compared with most procedures of peptide synthesis.
4. Losses and the frequency of false sequences are reduced, especially as compared with most carrier methods.
5. The mild and specific enzymatic removal of the peptide from the carrier with its possibility of yield and sequence control cannot be achieved with any purely chemical method.
6. In most cases suitable choice of the molecular weight of the polymer allows separation of trypsin and polymer from the cleaved peptide with its lower molecular weight by dialysis.

7. In contrast to the liquid phase method which uses the carrier polyethyleneglycol and therefore amino acid esters sensitive to alkali, the present method proceeds without peptide cleavage even at pH 11.

Further objects and advantages of the invention will become apparent from the following detailed description of a preferred embodiment with reference to the drawings, in which.

Figure 1:
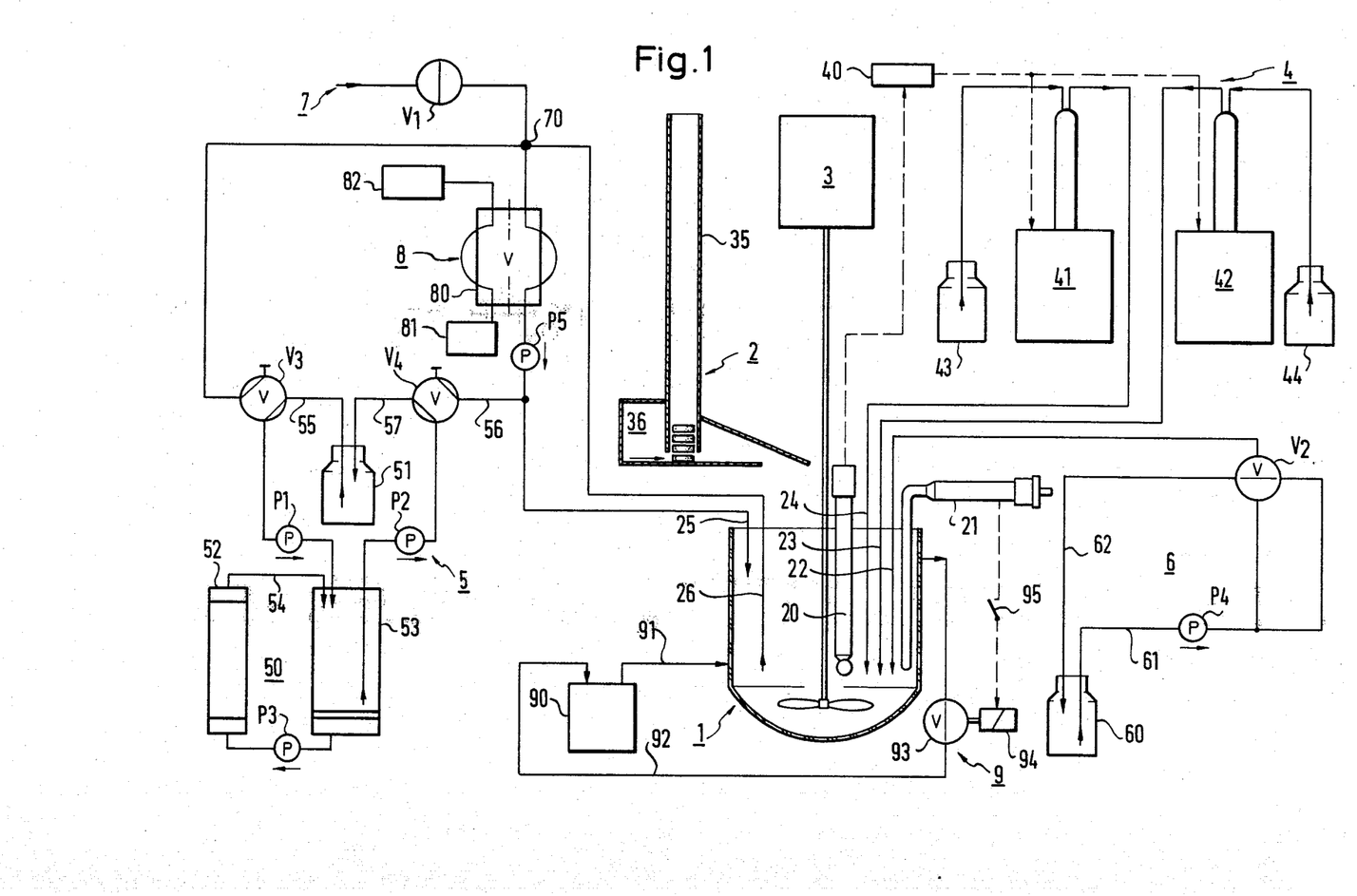
FIG. 1 is a diagram of an apparatus according to the invention for carrying out the process of the invention.
Figure 2:
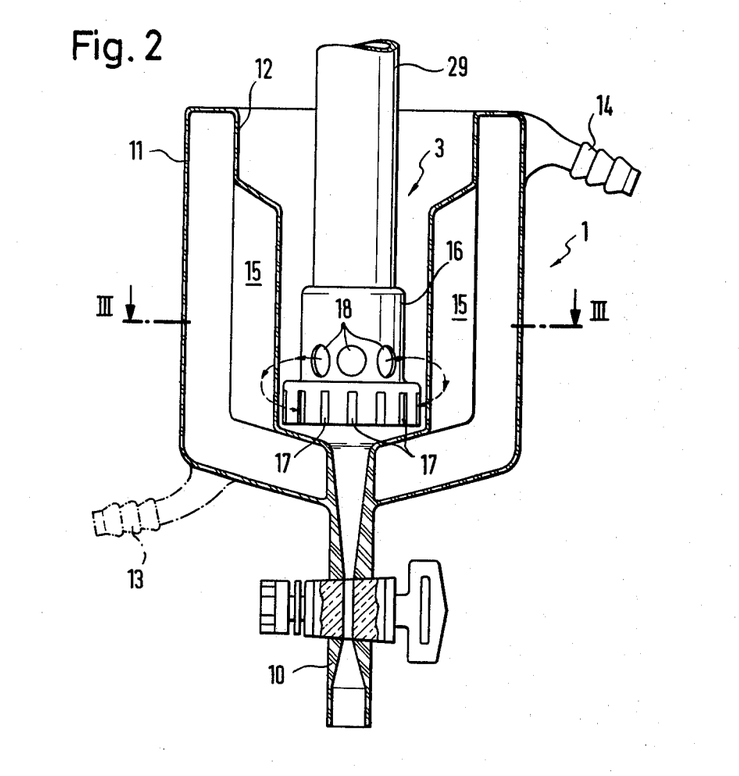
FIG. 2 depicts a reaction chamber as used in the apparatus of FIG. 1, shown in an axial section along the line II—II of FIG. 3.

The apparatus of the invention shown in FIG. 1 essentially comprises a reaction chamber 1, a device 2 for introducing the solid N-carboxyanhydrides of the amino acids into the reaction chamber, a mixer 3, a device 4 for controlling the pH value of the reaction liquid, a cooling means 9 for bringing the reaction liquid to a suitable temperature, a device 5 for purifying the desired high molecular end-product from low molecular by-products not fixed to the carrier, a supply 6 for liquid reagents, a gas supply 7, a sampling device 8, a device for controlling the timing of the reaction and means for supplying the titrating agents used.

The reaction chamber 1 including the mixer 3 is shown in detail in FIGS. 2 to 5. According to FIGS. 2 and 3, the reaction chamber consists of a double-walled vessel, a discharge pipe 10 with a valve being provided at the lower end of the vessel. The space between the outer wall 11 and the inner wall 12 serves for tempering the reaction liquid contained in the vessel and is connected to the cooling means by an inlet 13 and an outlet 14. As particularly shown in FIG. 3, both walls 11 and 12 of the vessel are circular-cylindrical with the inner wall 12 being provided with a number of, for example four, axially extending indentations or ribs 15. The indentations 15 assist the agitation and cause a motion of the reaction liquid in substantially vertical planes of circulation.

The mixer 3 for agitating the reaction liquid is coaxially disposed within the reaction chamber 1 and comprises a highspeed mixer available under the name "Ultra-Turrax" with its rotational speed being adjustable in two steps with freely selectable speeds up to 10,000 rpm. As indicated by the arrows in FIG. 2, the reaction liquid is drawn in by the rotor disposed inside the mixer through slots 17 provided at the lower end of the mixer housing 16 and is again emitted through openings 18 provided above the slots 17.

Figure 3:
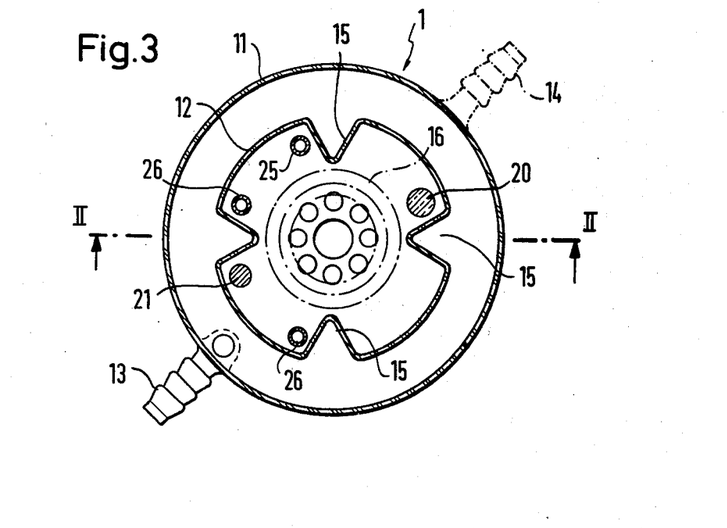
FIG. 3 is a cross-section of the reaction chamber along the line III—III of FIG. 2.

According to FIGS. 1 and 3, the reaction chamber 1 contains in addition to the mixer 3, a glass electrode 20, a thermometer probe 21 and various feeding and discharging tubes 22 to 26. These elements connect the reaction chamber 1 to the devices 4 to 9 and are located inside the reaction chamber within the individual spaces formed by the inner wall 12 of the chamber, the indentations 15 and the mixer housing 16.

Figure 4:
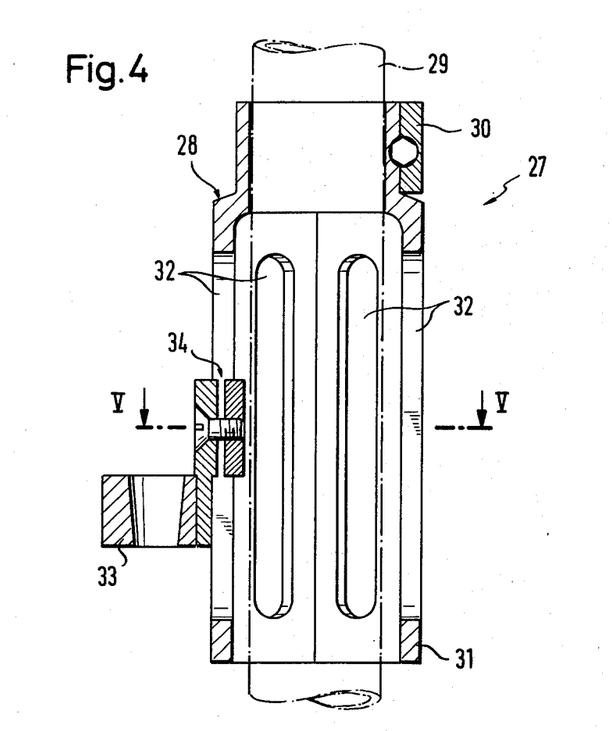
FIG. 4 shows a holding means for use with the reaction chamber of FIGS. 2 and 3.
Figure 5:
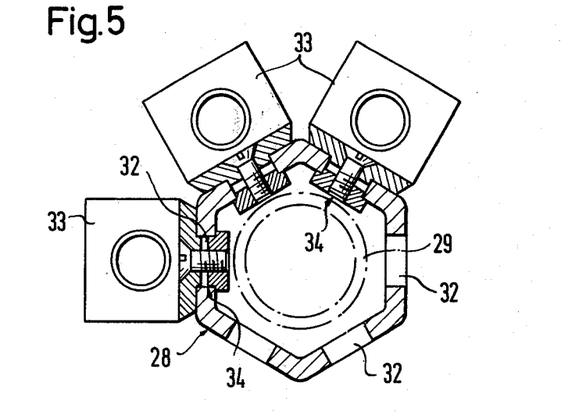
FIG. 5 is a cross-section through the holding means along the line V—V of FIG. 4.

In FIGS. 4 and 5, a holding arrangement 27 is shown for holding the various elements 20 to 26 so that they are immersed into the reaction liquid without contacting the mixer housing 16 or the inner wall 12 of the chamber. The holding arrangement 27 includes a sleeve 28 which is placed around a tube 29 of the mixer 3 leading out of the reaction chamber 1 and is fixed thereto at its upper cylindrical portion 30 by a clamping means. The lower portion 31 of the sleeve 28 has a polygonal, e.g. hexagonal, shape with the inner surfaces of the polygon being spaced from the tube 29. In each face of the polygonal lower portion 31 there are provided elongate slots in each of which a console 33 is adjustable in any desired heigth by means of a further screw-clamping means 34. The consoles 33 are provided with slightly conical bores for receiving the elements 20 to 26.

The device 2 for introducing the solid N-carboxyanhydrides of the amino acids into the reaction chamber 1 includes a vertical tubular tablet magazine 35 which comprises the weighed N-carboxyanhydrides of the amino acids in sealed capsules stacked upon each other in the sequence in which they are later-on to be linked to form the desired peptide, so that an automatic synthesis of the compounds: amino acid$_n$... — amino acid$_1$ — arginine — polyethyleneimine may be carried out at normal room temperature and humidity, taking into account the different stabilities of the individual N-carboxyanhydrides. The respective lowest capsule is introduced by means of an electromagnetic shooting mechanism 36 into the reaction chamber where it is crushed by the high-speed mixer 3, which results in a distribution of the reagent advantageous to achieve a high reaction It is important that the substances are introduced into the reaction chamber 1 in the form of tablets, capsules or the like. It is impossible to solve the substances in liquids because they would decompose. Also, the use of tablets or capsules allows an accurate dosing of the substances. In order to introduce the prescribed different amounts into the reaction chamber 1 at the proper moments during the process, the shooting mechanism 36 is controlled such that it is possible to eject from the magazine several tablets or capsules one after the other with short intervals, if required.

The device 4 for controlling the pH value of the reaction liquid, i.e. the titrating apparatus, includes the above mentioned low-temperature glass electrode 20 having a temperature feeler and a pH measuring device, a proportional-differential controller 40 with three selectable set values, for example for the pH values 10.2, 7.0 and 3.5, and adjustable in accordance with the control characteristic, as well as means for introducing the titration agent into the reaction liquid, which means are formed by the tubes 23, 24. The device 4 includes two automatic burettes 41, 42, i.e. vessels into which a motor-driven rigid displacement body is inserted to feed the contents of the vessels through the tubes 23, 24 into the reagent. As the titrating agents, caustic soda solution is contained in one vessel and sulphuric acid in the other one. A supply tank 43, 44 is connected to each burette 41, 42, respectively, by a corresponding line.

The tubes 23, 24 lead into the reagent close to the glass electrode 20 in an area of the reaction chamber 1 in which a suitable current is achieved by the mixer 3 so that the glass electrode operates reliable even at high rotational speeds.

The device 5 for purifying the high molecular endproduct from undesired low molecular products not fixed to the carrier comprises a pumping system having a valve V3 for discharging the reagent from the reacting chamber 1, a peristaltic pump P1, a dialyzer 50, a valve V4 for recycling the purified reagent into the reaction chamber 1, a further peristaltic pump P2 and a vessel 51 containing a rinsing liquid for the dialyzer 50 and the tube system. The dialyzer 50 is available as such by the firm Amicon under the name "Hollow-Fiber" and substantially consists of a diafiltration device 52, a supply tank 53 and a peristaltic pump P3 inserted in the connection between the outlet of the supply tank 53 and the inlet of the device 52. The outlet of the device 52 is connected via a further line 54 back to the supply tank 53 to form a closed circuit which allows the pump P3 to cycle the reagent through the dialyzer hollow fibers contained in the device 52, with water flowing around the exterior of the dialyzer hollow fibers. The dialyzer diaphragm is permeable to compounds of molecular weights below 10,000, according to the high polymer carrier used, i.e. arginyl-polyethyleneimine, which is purified by means of a corresponding dialyzer diaphragm (PM 10 diaphragm from Amicon).

Depending on its position, the valve V3 connects either the discharging tube 26 immersed in the reaction chamber 1 or the discharging line 55 of the vessel 51 to the inlet side of the pump P1 which accordingly pumps either the reaction liquid from the chamber 1 or the rinsing liquid from the vessel 51 into the supply tank 53 of the dialyzer 50. The other pump P2 feeds the contents of the supply tank 53 to the valve V4 which, depending on its position, feeds the respective liquid either via a line 56 and the feeding tube 25 into the reaction chamber 1 or via a line 57 into the vessel 51. In the position of the valves V3, V4 shown in FIG. 1, the vessel 51 containing the rinsing liquid is connected via the two pumps P1, P2 to the dialyzer 50 in a closed loop. In this position, the device 5 permits rinsing of the dialyzer. If both valves V3, V4 are switched-over to their other positions, the reaction liquid from the chamber 1 is fed through the dialyzer 50 and purified therein in accordance with the purpose of the dialyzer. The device 6 includes a supply tank 60 having a discharge line 61 and an input line 62, a peristaltic pump P4 and a valve V2. In the position of the valve V2 shown in FIG. 1, the discharge line 61 is connected to the input line 62 so that in operation of the pump P4 the reagent contained in the supply tank 60 is recycled. In its other position, the valve V2 connects the discharge line 61 to the tube 22 leading to the reaction chamber 1 so that in operation of the pump P4 the reagent from the tank 60 is introduced into the reaction liquid.

The gas supply 7 for introducing a gas into the reaction liquid comprises a nitrogen pressure bottle (not shown) having a pressure reducing valve adjusted to about 15 psi and an inlet valve V1 through which the gas may be introduced into the tube system at the junction 70.

The sampling device 8 essentially comprises a further pump system including a peristaltic pump P5 and a valve 80 with at least eight positions. The valve 80 includes a suitable rotatable hose magazine the individual hoses of which are switched, depending on the position of the valve, into the connection between the junction 70 and the peristaltic pump P5 or into a further connection between a pressurized-air source 81 and a sampling point 82. For sampling, reagent from the reaction chamber 1 is sucked by means of the pump P5 via the discharging tube 26 and the junction 70 into the respective hose of the valve 80, whereupon the magazine is rotated correspondingly and the contents of this hose is forced out of the valve to the sampling point 82 by the air from the pressurized-air source 81.

The connection of the device 8 shown in FIG. 1 enables the hose magazine to be rinsed with nitrogen or with the rinsing agent contained in the vessel 51 before and/or after each sampling by correspondingly positioning the valves V1, V3, V4 and operating the peristaltic pumps P1, P2, P5.

The cooling means 9 comprises a cooling aggregate 90 ("Kryomat") which contains methanol cooled to $-30°C$ and which is connected via lines 91, 92 to the inlet 13 and, respectively, the outlet 14 of the outer chamber surrounding the reaction chamber 1 between the outer wall 11 and the inner wall 12 thereof. A valve 93 is provided in the return line 92 and is controlled by the thermometer probe 21 and a relay 94. With the valve 93 in its open position, the coolant flows around the reaction chamber 1 and the reaction liquid is cooled until the valve 93 is closed by the thermometer probe 21. It will be understood that the reaction liquid is warmed up by the mixer 3 so that no separate heating system for the reaction liquid is required. A switch 95 is connected between the temperature probe 21 and the relay 95 for externally switching on and off the temperature control. All pumps P1 to P5 described above and shown in FIG. 1 form a common peristaltic pump having multiple sections and a commmon drive. This pump preferably operates continuously while only the valves V1 to V4 and 80 are controlled in accordance with the respective requirements of the synthesizing process.

Figure 6:
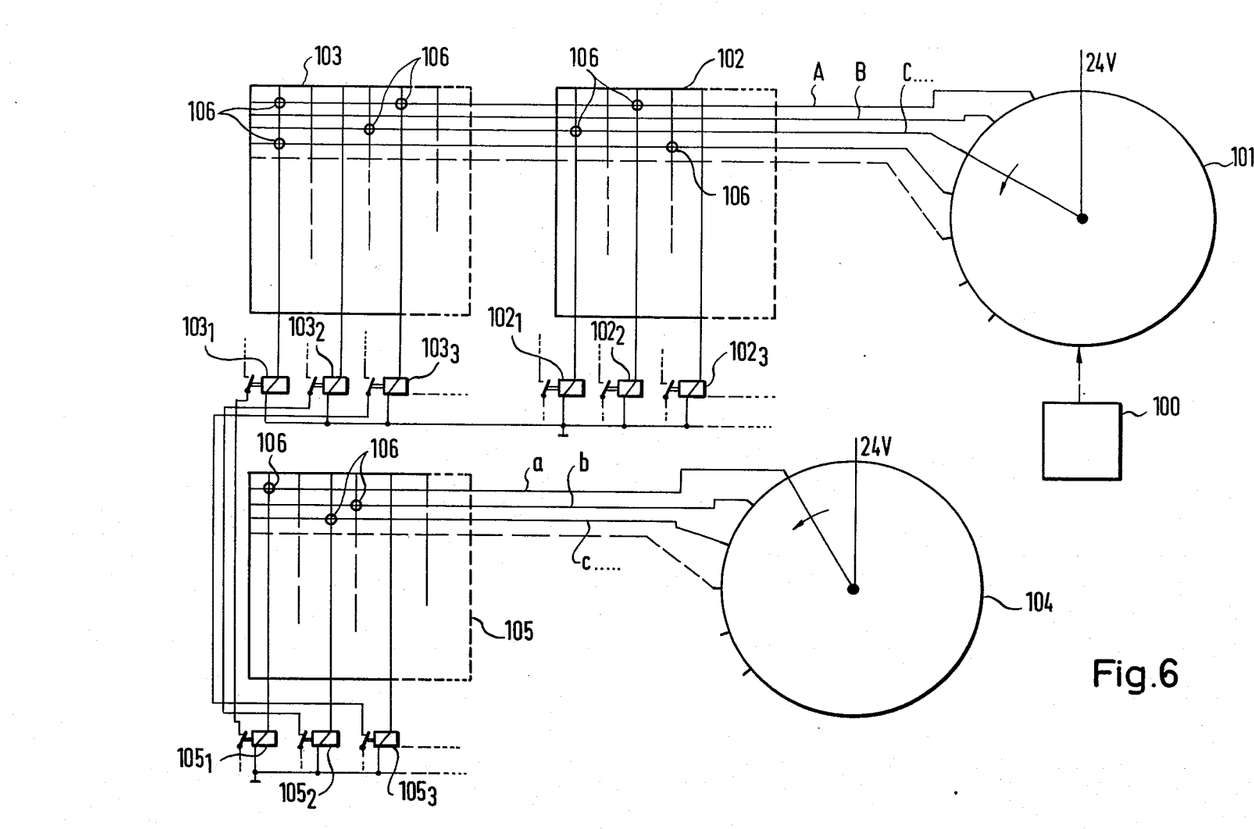
FIG. 6 shows a diagram of a control circuit.

FIG. 6 shows a control circuit for automatically controlling the entire process. A digital clock 100 indexes a first step-by-step switch 101 by one step whenever the digital actual time coincides with a preset digital value. The switch 101 has a number of outputs equal to the number of its possible positions (for instance twenty) and identified in FIG. 6 by capital letters A, B, C . . . According to its position, the switch 101 supplies its input voltage of for instance 24 volts to the respective output. The outputs A, B , C . . . are connected to the line bars of two junction boxes or crossbar distributors 102 and 103 arranged one behind the other, the column bars of which are each connected to relays $102_1$, $102_2$ . . . $103_1$, $103_2$ . . . Furthermore provided is a second step-by-step switch 104 which may be completely identical to the first step-by-step switch 101. Again, this second switch 104 feeds its input voltage of for instance 24 volts to the respective output corresponding to its position, the outputs of the second step-by-step switch being identified in FIG. 6 by small letters a, b, c . . . The outputs a, b, c . . . are connected to the line bars of a third crossbar distributor 105 which may be identical to the crossbar distributors 102, 103 and which has its column bars each connected to a relay $105_1$, $105_2$ . . . The coupling between the line and column bars of the three crossbar distributors 102, 103 and 105 is made by means of diode plugs or connectors 106 which are shown diagrammatically in FIG. 6. Similar to the preset digital values of the digital clock 100, the position of the diode connectors 106 on the crossbar distributors depends on the respective program to be performed for the process. All relays $102_1, 102_2 \ldots 103_1, \ldots 105_1, \ldots$ are connected to actuate on/off contacts for controlling the various control devices in the system of FIG. 1. One such contact is for instance assigned to the shooting mechanism 36 in the introducing device 2, to the valves in the device 4 for controlling the pH value, to the valves V1 to V5, to the sampling valve 80 and to the cooling means 9 (in the form of the above-mentioned switch 95).

While the step-by-step switch 101 is controlled by the digital clock 100 only as a function of time, as explained above, the second step-by-step switch 104 indexes by one step each time the first switch 101 returns to its start position. It is understood that the first step-by-step switch 101 does not necessarily perform all steps; instead, it is reset to its start position upon reaching a correspondingly programmed position.

Furthermore, while the contacts of the relays $102_1, 102_2 \ldots$ are directly connected to the corresponding control elements, the contacts assigned to the crossbar distributor 103 are connected in series with the contacts assigned to the crossbar distributor 105. The contacts of the relays $103_1$ and $105_1$ thus form a logical AND connection so that the corresponding control element is actuated only if the relay $103_1$ and the relay $105_1$ are energized. Similarly, the contacts of the relays $103_2$ and $105_2$ form an AND connection etc. This circuitry ensures that the functions controlled by the relays $102_1, 102_2 \ldots$ are actuated merely as a function of time depending on the step-by-step switch 101 which is controlled by the digital clock 100, while the functions controlled by the AND-connected relays $103_1$ and $105_1, 103_2$ and $105_2 \ldots$ are performed in dependence on the respective step of the synthesis, i.e. on the respective in dependence position of the step-by-step switch 104. The switch 101 thus determines the time sequence of the individual functions within one synthesis step, while the switch 104 selects the functions to be performed within each synthesis step.

The following examples are given for a more precise description of the invention.

EXAMPLE 1

An example for practising the invention is the synthesis of the peptide alanyl-tryptophanyl-isoleucine by synthesis of the peptide alanyl-tryptophanyl-isoleucyl-arginine on the carrier, the subsequent enzymatic cleavage of this peptide with trypsin from the carrier, and the removal of arginine from its carboxyl end with carboxypeptidase B.

SYNTHESIS OF ARGINYL-POLYETHYLEMEIMINE (SCHEME 1)

Commercial polyethyleneimine 1 is first dialyzed for 72 hours against 2×4 liters of twice distilled water in an Amicon PM 10 membrane to remove polymer of molecular weight ≤ 10,000. 2.581 g (60 mmoles) of polymer cut in this fashion are dissolved in 150 ml of 0.4 M borate buffer titrated to pH 10.2 with 4 N sodium hydroxide. The solution is stirred at 10,000 rpm with an Ultra Turrax mixer using a TG 45 mixing head manufactured by Janke and Kunkel, Staufen, Western Germany. Two drops of n-octanol serve as anti-foaming agent. After cooling the polymer solution to 0°C (cooling jacket temperature −30°C, see below) 10 ml of a solution of the N-carboxyanhydride of arginine in absolute dimethylformamide obtained from 5.474 g (14.06 mmole) of alpha-carbobenzoxy-L-arginine hydrobromide are dripped into the stirred polymer over a period of 3 minutes. The pH is held at 10.2–0.1 with 4 N sodium hydroxide for 5 minutes, then brought to 3.0 with 10% sulfuric acid and, after 0.5 minutes, is raised to 7.0 with 4 N sodium hydroxide. The entire reaction takes place in a 300 ml glass vessel equipped with cooling jacket, drain at the bottom, four vertical glass ridges inside, a thermometer and a pH meter. Water, n-octanol and dimethylformamide are removed by lyophylization. The product is redissolved in 200 ml of water and ultrafiltered for 24 hours against 3×4 liters of water in a Hollow-fiber Cartridge H1 DP 10 made by Amicon, Oosterhout, Holland, set for "dialysis". Lyophylization of the dialysate and subsequent drying in a vacuum of 20 Torr at 65°C for 12 hours yield 7.002 g of an arginylated polyethyleneimine sulfate 3. Gravimetric sulfate determination reveals a sulfate content of 30.4 % with a calculated degree of arginylation of 50.4 weight %, or 16.05 mole %. Since 9.63 mmole of the N-carboxyanhydride of arginine hydrobromide react with 60 mmole of polyethyleneimine, statistically every 6–7th functional group containing nitrogen (or every second amino group) of the polymer has been arginylated.

SYNTHESIS ON THE CARRIER POLYMER (SCHEME 2)

SYNTHESIS OF ISOLEUCYL-ARGININE-POLYETHYLENEIMINE (5)

0.395 g Of arginyl-polyethyleneimine 3 (0.80 mmole, arginine, 30.4 % sulfate) are allowed to react with 0.157 g of the pulverized N-carboxyanhydride of isoleucine 4 (1.0 mmole, molar proportion of isoleucine : arginine = 1.25 : 1) in a fashion analogous to the synthesis of arginyl-polyethyleneimine, and are dialyzed for 24 hours until a negative ninhydrin reaction of the ultrafiltrate results. The solution is subsequently concentrated to 20 ml in an Amicon Ultrafiltration Chamber Type 202 fitted with an Amicon PM 10 membrane, diluted to 150 ml with 0.4 M borate buffer, and without further manipulations processed to yield product 7.

SYNTHESIS OF TRYPTOPHANYL-ISOLEUCYL-ARGINYL-POLYETHYLENEIMINE (7)

Product 5 is allowed to react with 0.230 g (1.0 mmole) of the pulverized N-carboxyanhydride of tryptophane 6 in a fashion analogous to the synthesis of arginyl-polyethyleneimine 3 and prepared for reaction with the N-carboxyanhydride of alanine 8.

SYNTHESIS OF ALANYL-TRYPTOPHANYL-ISOLEUCYL-ARGINYL-POLYETHYLENEIMINE (9)

Product 7 is allowed to react with 0.115 g (1.0 mmole) of the pulverized N-carboxyanhydride of alanine as described in the synthesis of 5. Ultrafiltration of 9 is followed by lyophylization.

ENZYMATIC CLEAVAGE OF THE PEPTIDE FROM THE CARRIER (SCHEME 2)

ALANYL-TRYPTOPHANYL-ISOLEUCYL-ARGININE (10)

TRYPTOPHANYL-ISOLEUCYL-ARGININE (11)

5×5.25 mg Of (9) are dissolved in 0.5 ml of 0.02 M $CaCl_2$ in 0.05 M Tris buffer, pH 8.0 and incubated for 2 hours at 27°C with 1mg of tosylphenylalanine-chlorketone treated trypsin dissolved in 0.01 ml of 0.001 M HCl. The samples are then lyophylized, dissolved in 0.2 ml of methanol, applied to five thin layer chromatography plates (0.2 mm layer of silica gel on glass) and chromatographed in a butanol/glacial acetic acid/water solvent system (4 volumes butanol : 1 volume glacial acetic acid : 2 volumes water). Elution of the bands with $R_f$ values of 0.39 yielded 0.27 mg of product 10 each, of those with $R_f = 0.43$ yielded 0.32 mg of product 11 each, as determined spectroscopically at 280 nm.

Total yield of product 10 : 31.8%.
Total yield of product 11 : 37.8%.

ENZYMATIC CLEAVAGE OF THE ARGININE BRIDGES FROM THE PEPTIDE (SCHEME 2)

1 mg ($1.84 \times 10^{-6}$ mole) Of alanyl-tryptophanyl-isoleucyl-arginine and 1 mg of D-phenylalanine to inhibit carboxypeptidase A present in a concentration of approximately 1% in the carboxypeptidase B preparation, are dissolved in 0.4 ml of 0.025 M Tris buffer, pH 7.5, and incubated for 1 hour at 27°C with 12.7 micrograms of carboxypeptidase B (0.1 ml of carboxypeptidase B per 0.02 ml of suspension, are added to 1.02 ml of 10% LiCl). Following lyophylization alanyl-tryptophanyl-isoleucine (product 12, $R_f = 0.61$) and arginine 13 are separated by thin layer chromatography using a butanol/glacial acetic acid/ water solvent system (4:1:2).

EXAMPLE 2

This example shows a typical synthesis procedure. Approximately 130 ml of saturated borate solution and an amound of arginylpolyethyleneimine (corresponding to $10^{-3}$ moles of arginine at the polymer) are introduced into the reaction chamber. From the amino acids to be linked, $10^{-3}$ moles (or an excess, depending on the reactivity) of the N-carboxyanhydride to be reacted are weighed into capsules and filled into the magazine. The following program is started by pushing a button:

1. Cooling to 0°C at low agitation.
2. Titrating to pH 10.2 (with 50% NaOH).
3. Shooting one or a number of capsules with the respective NCA-amino acid at maximum agitating speed and reacting five minutes.
4. Heating and titrating to pH 3.5 (with 50% $H_2SO_4$) and introducing nitrogen for $CO_2$ degassing.
5. Diafiltration.
6. Titrating to pH 7.
7. Sampling.
8. Restart at (1) or stop.

The program includes functions of time as well as functions of time and process step.

While the above provides a full and complete disclosure of the invention, it is understood that various modifications, alternate constructions and equivalents may be employed without departing from the true spirit and scope of the invention. Accordingly, the above description and illustrations should not be construed as limiting the scope of the invention, which is solely defined by the appended claims.

What is claimed is:

1. A method for synthesizing polypeptides employing N-carboxyanhydrides of amino acids which comprises:
    1. combining in an aqueous alkaline medium a water soluble poly(monopeptide)-polyethyleneimine, consisting of polyethyleneimine of at least about ten thousand molecular weight and arginine bonded to said polyethyleneimine by amide linkages, with an N-carboxyanhydride to form a poly(-dipeptide)-polyethyleneimine having terminal carbamyl groups;
    2. acidifying said medium to hydrolyse said terminal carbamyl groups to amino groups;
    3. freeing said medium of lower molecular weight compounds;
    4. repeating steps (1) to (3) to form a poly(n-peptide)-polyethyleneimine from a poly((n-1)peptide)-polyethyleneimine; and
    5. enzymatically cleaving said poly(n-peptide)-polyethyleneimine to form an arginyl carboxy end group substituted poly(n-peptide) and enzymatically cleaving said arginyl group to leave said (poly(n-peptide).

2. A method according to claim 1, wherein said lower molecular weight compounds are removed from said medium by dialysis.

3. A method according to claim 2, wherein said enzymatic cleaving is carried out at a temperature in the range of about 0°–50°C for a time in the range of about 10 minutes-24 hours at a pH in the range of about 7–9.

4. A method according to claim 1, wherein said enzymatic cleaving is carried out at a temperature in the range of about 0°–50°C, for a time in the range of about 10 minutes to 24 hours, and at a pH in the range of about 7–9.

5. A method according to claim 1, wherein said poly(monopeptide)-polyethyleneimine has about one arginine group per two amino groups present in said polyethyleneimine.

6. A method according to claim 1, wherein said arginyl carboxyl end group substituted poly(n-peptide is cleaved with carboxypeptidase B to remove the arginyl group.

7. A method according to claim 6 wherein said arginyl carboxy end group substituted n-peptide is cleaved from said polyethyleneimine with tosyl-phenylalanine-chlorketone treated trypsin.

8. A method according to claim 1, wherein at least one of said N-carboxyanhydrides is combined in said medium as a solid tablet or capsule with substantial agitation, whereby said tablet or capsule is disintegrated.

9. A method according to claim 1, wherein said aqueous alkaline medium is at a pH of about 10.2 and said acidification is carried out to a pH in the range of about 3–4.

10. A method according to claim 1, wherein said combining is carried out at a temperature in the range of about 0°–30°C.

* * * * *